(12) United States Patent
Mormul et al.

(10) Patent No.: US 10,407,534 B2
(45) Date of Patent: Sep. 10, 2019

(54) CYCLIC CARBONATES

(71) Applicant: BASF SE, Ludwigshafen (DE)

(72) Inventors: Verena Mormul, Mannheim (DE); Rainer Klopsch, Worms (DE); Miran Yu, Worms (DE); Guenter Scherr, Ludwigshafen (DE); Diego Ghislieri, Heppenheim (DE)

(73) Assignee: BASF SE, Ludwigshafen (DE)

( * ) Notice: Subject to any disclaimer, the term of this patent is extended or adjusted under 35 U.S.C. 154(b) by 122 days.

(21) Appl. No.: 15/567,513

(22) PCT Filed: Apr. 15, 2016

(86) PCT No.: PCT/EP2016/058418
§ 371 (c)(1),
(2) Date: Oct. 18, 2017

(87) PCT Pub. No.: WO2016/169858
PCT Pub. Date: Oct. 27, 2016

(65) Prior Publication Data
US 2018/0112030 A1   Apr. 26, 2018

(30) Foreign Application Priority Data

Apr. 23, 2015 (EP) .................................. 15164849

(51) Int. Cl.
| | | |
|---|---|---|
| *C08G 59/40* | (2006.01) | |
| *C07D 317/40* | (2006.01) | |
| *C07D 407/06* | (2006.01) | |
| *C08G 59/24* | (2006.01) | |
| *C08G 59/56* | (2006.01) | |
| *C08G 59/50* | (2006.01) | |

(52) U.S. Cl.
CPC ....... *C08G 59/4007* (2013.01); *C07D 317/40* (2013.01); *C07D 407/06* (2013.01); *C08G 59/245* (2013.01); *C08G 59/504* (2013.01); *C08G 59/5026* (2013.01); *C08G 59/56* (2013.01)

(58) Field of Classification Search
CPC .... C08F 222/20; C08F 224/00; C08F 220/18; C08F 226/00; C08F 2220/283; C08F 2220/1825; B32B 27/00; B32B 27/08; B32B 27/32; B32B 27/36; B32B 37/12; B32B 7/00; B32B 7/12; B32B 2037/1269; C08G 71/04; C08G 59/56; C08G 59/245; C08G 59/5026; C08G 59/504; C08G 59/4007; C09D 135/02; C09D 11/107; C09J 135/02; C07D 407/06; C07D 317/40

See application file for complete search history.

(56) References Cited

U.S. PATENT DOCUMENTS

| | | |
|---|---|---|
| 3,781,379 A | 12/1973 | Theodore et al. |
| 4,091,048 A | 5/1978 | Labana et al. |
| 2003/0100687 A1 | 5/2003 | Ohrbom et al. |
| 2013/0331532 A1* | 12/2013 | Porta Garcia .......... C08F 24/00 526/269 |

FOREIGN PATENT DOCUMENTS

| | | |
|---|---|---|
| DE | 27 49 576 A1 | 5/1979 |
| WO | WO 03/048215 A1 | 6/2003 |
| WO | WO 2011/157671 A1 | 12/2011 |
| WO | WO 2013/050311 A1 | 4/2013 |
| WO | WO 2013/144299 A1 | 10/2013 |

OTHER PUBLICATIONS

International Search Report and Written Opinion dated May 24, 2016 in PCT/EP2016/058418 filed Apr. 15, 2016 (with English translation).

* cited by examiner

*Primary Examiner* — Christopher M Rodd
(74) *Attorney, Agent, or Firm* — Oblon, McClelland, Maier & Neustadt, L.L.P.

(57) ABSTRACT

Compounds of the formula

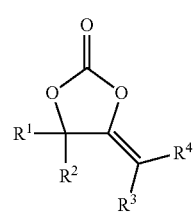

(I)

in which
$R^1$ is an organic radical having a (meth)acryloyl group and $R^2$, $R^3$, and $R^4$ independently of one another are an H atom or a C1 to C10 alkyl group.

13 Claims, No Drawings

CYCLIC CARBONATES

The invention relates to compounds of the formula

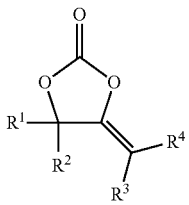

(I)

in which
R¹ is an organic radical having a (meth)acryloyl group and R², R³, and R⁴ independently of one another are an H atom or a C1 to C10 alkyl group, and to their use in epoxy resin compositions.

Compounds having a cyclic carbonate group and their use in epoxy resin compositions are described in WO 2011/157671 and WO 2013/050311.

WO 2013/050311 discloses compounds having a cyclic carbonate group which are substituted by an electron-withdrawing group, more particularly a carboxyl group.

WO 2011/157671 discloses a cyclic carbonate compound having a double bond directly on the ring system, also referred to as exo-vinylene carbonate. The exo-vinylene carbonate likewise comprises radicals R¹ to R⁴; see compound I of WO 2011/157671. None of the radicals R¹ to R⁴, however, can comprise a (meth)acryloyl group. Cyclic carbonate compounds identified and used specifically in WO 2011/157671 are only compounds which are not polymerizable.

Compounds having a cyclic carbonate group and having a polymerizable double bond are known from WO 2013/144299. The polymerizable double bond here is bonded via a spacer to the exo-vinylene group of the exo-vinylene carbonate of WO 2011/157671. The cyclic carbonate compounds of WO 2013/144299 are polymerized and, as polymers or copolymers, find a host of different uses.

Epoxy resins are typically compounds having on average more than one epoxide group per molecule. They can be converted into polymers by reaction with suitable hardeners. On the basis of their good performance properties, such as high impact strength, high abrasion resistance, good chemical resistance, high resistance in the face of alkalis, acids, oils, and organic solvents, epoxy resins find diverse uses, as coating materials or adhesive, for example.

For epoxy resins, a low viscosity is advantageous to their use. Low viscosities permit low temperatures on use, generally facilitate the processing techniques, and lead in general to good results—in particular, uniform coatings and uniform moldings.

The uncured epoxy resins are therefore frequently admixed with diluents, which reduce the viscosity of the resin to the level desired for the application. Suitable diluents are, in particular, reactive diluents. Reactive diluents are solvents which have functional groups that react with the epoxide groups of the resin and/or with the functional groups of the hardener to form covalent bonds.

The aforementioned WO 2013/050311 and WO 2011/157671 relate to the use of the disclosed cyclic carbonates as reactive diluents in such epoxy resins.

A fundamental object in relation to the prior art is to find alternative diluents for epoxy resin compositions, these diluents lowering the viscosity and further improving, or at least not adversely affecting, the performance properties, especially the reactivity. Of particular interest in this context are diluents which can be obtained by an efficient and cost-effective preparation process.

It was an object of the present invention, accordingly, to provide such diluents.

The compounds defined at the outset have been found accordingly. Also found has been a preparation process for these compounds.

The compounds of the formula (I)

In formula (I), R¹ is an organic radical having a (meth) acryloyl group.

R², R³, and R⁴ independently of one another are an H atom or a C1 to C10 alkyl group. Compounds of the formula I are also referred to as hereinafter as ExoVC (meth)acrylates.

Preferably, R¹ is an organic radical having a total of not more than 24 C atoms, more particularly not more than 18 C atoms, and very preferably not more than 14 C atoms. R¹ may comprise further heteroatoms in addition to oxygen, such as nitrogen or sulfur.

In one particular embodiment, R¹ consists exclusively of carbon, hydrogen, and oxygen, and therefore comprises no heteroatoms other than oxygen atoms. Oxygen atoms are found in the acryloyl group or methacryloyl group, (meth) acryloyl group for short, and optionally in further functional groups such as ether groups, hydroxyl groups, or carbonyl groups. In particular, R¹ comprises oxygen in the (meth) acryloyl group and otherwise only in any ether groups present.

More preferably, R¹ is one of the groups below of the formula (II), (III), or (IV).

In formula (II)

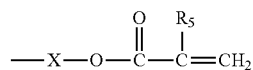

X is a bond or an alkylene group having 1 to 18 C atoms, and R⁵ is an H atom or a methyl group.

X is preferably an alkylene group having 1 to 18 C atoms.

The alkylene group may be a linear or branched alkylene group.

With particular preference it is an alkylene group having 1 to 10 C atoms. More particularly it is a linear C1 to C10 alkylene group. In one particular embodiment it is a linear C2 to C8 alkylene group. More particularly it is a linear C2 to C6 alkylene group, as for example an ethylene, n-propylene, or n-butylene group; very preferably, X is an n-propylene group.

In formula (III)

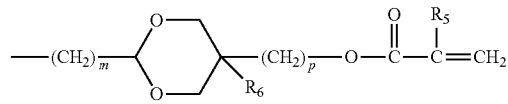

m and p independently of one another are 0 or an integer from 1 to 10, R⁵ has the above definition, and R⁶ is an H atom or a C1 to C10 alkyl group.

Preferably, m is an integer from 1 to 10, more particularly an integer from 1 to 6, and very preferably m is 1.

Preferably, p is 0 or an integer from 1 to 6, more particularly p is an integer from 1 to 6, and very preferably p is 1.

In one particular embodiment, m and p independently of one another are an integer from 1 to 6. In one especial embodiment both m and p are 1.

$R^6$ is preferably an H atom or a C1 to C6 alkyl group. In one particular embodiment, $R^6$ is a C1 to C6 alkyl group, as for example a methyl group or ethyl group, more particularly an ethyl group.

In formula (IV)

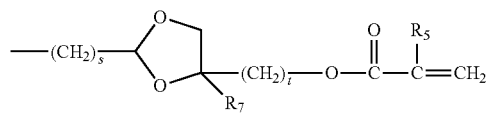

s and t independently of one another are 0 or an integer from 1 to 10, $R^5$ has the above definition, and $R^7$ is an H atom or a C1 to C10 alkyl group.

Preferably, s and t independently of one another are an integer from 1 to 10, more particularly an integer from 1 to 6. In one particular embodiment, both s and t are 1.

$R^7$ is preferably an H atom or a C1 to C6 alkyl group. In one particular embodiment, $R^7$ is an H atom.

In the compounds of the formula I, $R^2$ is preferably an H atom or a C1 to C6 alkyl group. More particularly, $R^2$ is a C1 to C6 alkyl group, and very preferably is a methyl group.

In the compounds of the formula I, $R^3$ and $R^4$ independently of one another are an H atom or a C1 to C10 alkyl group. The alkyl group is more particularly a C1 to C6 alkyl group, preferably a C1 to C3 alkyl group, and, in one particular embodiment, a methyl group.

Preferably, at least one of the radicals $R^3$ and $R^4$ is an H atom.

More preferably, both $R^3$ and $R^4$ are an H atom, or one of $R^3$ and $R^4$ is an H atom and the other is an alkyl group, more particularly a methyl or ethyl group.

Especially preferably both $R^3$ and $R^4$ are an H atom.

In all compounds of the formula I, preferably, R5 is an H atom, and compounds of the formula I are therefore preferably acrylic compounds.

Particularly preferred compounds of the formula I are those in which $R^1$ is a group of the formula (II) or (III), more particularly a group of the formula (II).

Examples of compounds of the formula (1) include the following preferred compounds:

Compound of the formula I a:

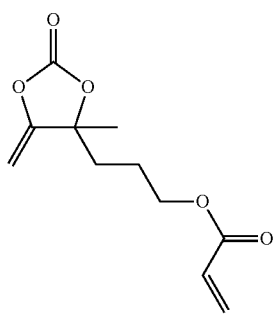 [SMILES: C=CC(=O)OCCCC1(C)OC(=O)OC1=C]

Compound of the formula I b:

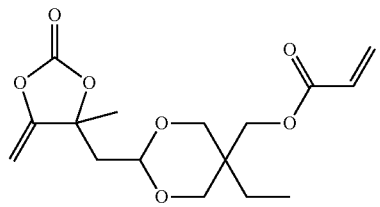 [SMILES: C=CC(=O)OCC1(CC)COC(CC2(C)OC(=O)OC2=C)OC1]

Compound of the formula I c:

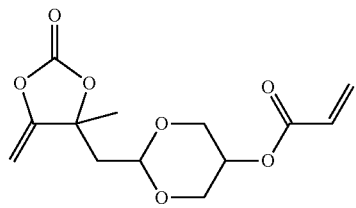 [SMILES: C=CC(=O)OC1COC(CC2(C)OC(=O)OC2=C)OC1]

and compound of the formula I d

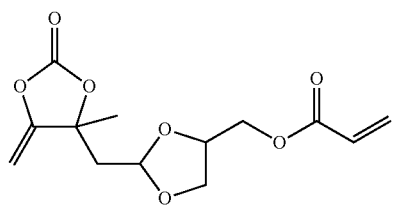 [SMILES: C=CC(=O)OCC1COC(CC2(C)OC(=O)OC2=C)O1]

Preparation of Compounds of the Formula (I) with $R^1$=Formula (II)

Compounds of the formula (I) with $R^1$=formula (II) may be prepared in particular by a process in which
- in a first stage, a compound having a terminal triple bond is reacted with a hydroxyalkanone or hydroxyalkanal, the triple bond undergoing addition to the carbonyl group of the hydroxyalkanone or hydroxyalkanal to form a dihydroxy compound,
- in a second stage, the hydroxyl group of the resulting dihydroxy compound that did not originate from the carbonyl group is protected with a protecting group,
- in a third stage, the ring closure to form the carbonate group takes place with carbon dioxide, and
- in a fourth stage, the protecting group is replaced by a (meth)acryloyl group.

Stage 1

The reaction of the first stage is a conventional addition of triple bonds to a carbonyl group.

Suitable compounds having a terminal triple bond are, in particular, compounds of the formula V

 Y—CH≡CH, where Y is an H atom, a hydrocarbon group having 1 to 10 C atoms, such as an alkyl or aryl group, or a protecting group having not more than 10 C atoms. Where Y is not a protecting group, the substituents of the Y-substituted C atom determine the subsequent radicals R3 and R4 in formula I. Starting from formula V, therefore, one of the radicals, R3 or R4, in formula I is an H atom, and the other is Y. The preferred definitions of Y therefore correspond to the above preferred definitions of R3 and R4, respectively.

Y, however, may also be a protecting group. Protecting groups are eliminated again during or after the synthesis has taken place, and so in this case the subsequent radicals R3 and R4 in the formula I are both an H atom. An example of a suitable protecting group is the trimethylsilyl group (TMS for short).

Preferred hydroxyalkanones or hydroxyalkanals are compounds of the formula VI

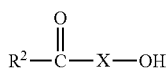

in which R2 is an H atom or a C1 to C10 alkyl group.

R2 corresponds to the R2 in formula I; in one preferred embodiment, R2 is a methyl group.

X corresponds to the X in formula II.

Statements have already been made above with regard to the preferred definitions of R2 and X.

For the implementation of the addition reaction there are various methods known. The starting compounds are preferably reacted in the presence of a strong base. Preferred strong bases are metal alkoxides. These are preferably metal salts of aliphatic alcohols, more particularly metal salts of C1 to C8, preferably C2 to C6, alcohols, such as ethanol, n-propanol, isopropanol, n-butanol, or tert-butanol. The metal cations of the metal alkoxides are preferably alkali metal cations, examples being the cations of sodium or potassium. Preferred metal alkoxides include, for example, potassium tert-butoxide, sodium tert-butoxide, potassium isopropoxide, and sodium isopropoxide.

The reaction is carried out preferably in the presence of a solvent. Preferred solvents are inert solvents; these comprise no reactive groups which react with the starting compounds. Particularly preferred are inert, polar, aprotic solvents. Examples of such include cyclic ether compounds, especially THF.

The reaction is generally exothermic, and cooling is therefore preferably applied during the reaction. The temperature of the reaction mixture is preferably not more than 50° C., more particularly not more than 25° C.; preferably it is situated between 0 and 25° C.

In order to work up the product mixture obtained, water, optionally acid, and optionally a nonpolar organic solvent may be added. If the desired product of the 1st stage already forms an independent organic phase, there is no need for the organic solvent. Two phases are formed, of which the organic phase comprises the product of the 1st stage (addition products). The organic phase can be dried in order to remove water. Solvents can be separated off easily by distillation. The product can be obtained in pure form by vacuum distillation.

Alternatively, working up may also take place according to customary methods of crystallization or extraction, particularly if the product of the 1st stage has a very high boiling point.

Stage 2

In the second stage, a hydroxyl group of the dihydroxy compound obtained is protected with a protecting group. The hydroxyl group which has originated from the carbonyl group is reacted with $CO_2$ in the third stage to form the carbonate ring. The hydroxyl group of the starting compound present even before the 1st stage (original hydroxyl group for short) is protected in order to avoid secondary reactions.

Particularly suitable protecting groups are ester groups. For this purpose, the original hydroxyl group is reacted with an acid or with an acid derivative. Preference is given to reaction with a carboxylic acid, formic acid or acetic acid for example, or, in particular, with a carboxylic acid derivative, such as a carboxylic anhydride, carboxylic ester, or carbonyl chloride, for example.

The original hydroxyl group is substantially more reactive than the hydroxyl group originating from the carbonyl group. In the esterification, therefore, initially only the ester of the original hydroxyl group is formed. The esterification is discontinued before any marked formation of ester with the other hydroxyl group is observed. The reaction can be monitored by means of gas chromatography.

The esterification may be carried out according to customary methods. In the course of the reaction, the temperature is preferably only raised slowly, allowing the progress of ester formation to be effectively monitored by chromatography, and allowing the reaction to be discontinued promptly.

Examples of possible temperatures for the reaction are from 0 to 100° C.; the temperature is preferably between 0 and 40° C.

The ester obtained may be purified by distillation. In the case of high boiling points, working up and purification by crystallization or extraction are also contemplated.

Stage 3

In a third stage, ring closure takes place with carbon dioxide to form the cyclic carbonate group.

For this purpose, carbon dioxide, preferably in gaseous form or in supercritical state, is contacted with the ester under superatmospheric pressure. The reaction is preferably carried out in an autoclave, therefore.

Carbon dioxide may also be used in a mixture with inert gas.

The reaction takes place preferably in the presence of catalysts. It takes place preferably in the presence of a base as catalyst or, more preferably, in the presence of a catalyst system composed of a base and of a metal salt. Preferred bases are compounds of at least one tertiary amino group, examples being those having one to three tertiary amino groups. Bases of this kind are known. They typically have a molar weight of below 500 g/mol, more particularly below 300 g/mol. More particularly they are aliphatic or cycloaliphatic compounds.

Examples of suitable bases include
TMTACN (N,N',N''-trimethyl-1,4,7-triazacyclononane),
PMDETA (pentamethyldiethylenetriamine),
TMEDA (tetramethylethylenediamine),
DBU (1,8-diazabicyclo[5.4.0]undec-7-ene), or
DBN (1,5-diazabicyclo[4.3.0]non-5-ene).

The metal salt preferably comprises salts having one to three valent cations, more particularly cations of Cu, Ag, or Au. The anion of the metal salts is preferably a carboxylate, more particularly a C1 to C6 carboxylate. Preferred metal salts include silver acetate or copper acetate.

Also contemplated as catalysts are phosphanes. These are, in particular, trialkyl- or triarylphosphanes. They can be used alone or likewise in combination with a metal salt.

The reaction is carried out preferably under a pressure of 1 to 100 bar, more particularly 5 to 70 bar. The temperature of the reaction mixture is preferably 10 to 100° C., more particularly 10 to 80° C. The reaction may be monitored by means of gas chromatography, for example.

After cooling and letdown of pressure, the resulting product (ExoVC ester) can be worked up. An organic solvent, preferably an inert, hydrophobic organic solvent such as dichloromethane or toluene, and aqueous acid, such as aqueous HCl, for example, may be added, so that two phases are formed. The organic phase comprises the desired product. Water can be removed from the organic phase by drying. Solvent may be removed by distillation. The product can be purified by means of distillation. A gentle and therefore preferred distillation is distillation, for example, in a thin-film evaporator. Particularly suitable for this purpose are thin-film evaporators with a wiper system.

An alternative option contemplated, where the third-stage product has high boiling points, is that of working up and purifying by crystallization or extraction.

Stage 4

In the 4th stage, the protected ExoVC, such as the ExoVC ester, obtained in the third stage is reacted with a (meth) acryloyl compound to give the ExoVC (meth)acrylate of the formula I.

A (meth)acryloyl compound used is, in particular, an alkyl (meth)acrylate, e.g., methyl (meth)acrylate. The protecting group, in this case the formate, is replaced by the (meth) acryloyl group, with the corresponding alkyl formate being released.

This reaction can be carried out by various methods known to the skilled person. It is preferably carried out enzymatically.

Suitable enzymes for this purpose are lipases. Lipases catalyze the breakdown of fat or formation of fat from fatty acids and glycerol, and are therefore also suitable as catalysts for esterifications or transesterifications or corresponding transesterification reactions in which two esters switch their radical of the alcohol used that originated from the esterification reaction.

An example of a suitable lipase is the enzyme *Candida Antarctica* Lipase B. The lipases are used preferably in an immobilized form. Immobilized lipases are those bound to a support. Suitable supports are natural organic polymers such as cellulose, synthetic organic polymers such as polystyrene, or inorganic substances such as clays or silicates.

The enzymatically catalyzed reaction may take place, for example, at a reaction mixture temperature of 0 to 100° C., preferably 20 to 80° C., more preferably 30 to 60° C. The reaction is carried out simply under atmospheric pressure; an increase in or lowering of pressure is not necessary, but is also not deleterious.

The reaction is an equilibrium reaction. Preferably, therefore, the compound released during the reaction is withdrawn from the mixture, whether by distillation, to remove the alkyl formate released, for example, or else by absorption, on a molecular sieve, for example.

The removal of the compound released may take place continuously, by a sustained reduced pressure, for example. Alternatively, the reaction may be interrupted after a certain time, for removal of the compound released, and thereafter continued again.

Lastly, the enzyme may be separated from the reaction mixture by filtration, and the mixture may be purified by distillative removal of the unreacted starting materials or by-products formed.

The reaction over all four stages proceeds overall with no problems and in a simple way, and is therefore also suitable for an industrial scale. The ExoVC (meth)acrylate is obtained with high yield and selectivity.

A schematic representation of the four stages is also found in preparation example 2.1.

Preparation of Compounds of the Formula (I) with $R^1$=Formula (III)

Compounds of the formula (I) with $R^1$=formula (III) may be prepared in particular by processes in which in a first stage, a compound having a terminal triple bond is reacted with an alkanone or alkanal which comprises an acetal group, the triple bond undergoing addition to the carbonyl group of the alkanone or alkanal to form a hydroxy compound, in a second stage, the ring closure to form the carbonate group takes place with carbon dioxide, in a third stage, the ring closure to form the 1,3-dioxane ring is carried out by reaction of the acetal group with a compound having a total of at least three hydroxyl groups, with two of the hydroxyl groups being located in 1,3 position, and in a fourth stage, the (meth)acryloyl group is introduced by esterification or transesterification of the remaining hydroxyl group.

Stage 1

The reaction of the first stage is a conventional addition of triple bonds to a carbonyl group.

Suitable compounds having a terminal triple bond are, in particular, compounds of the formula V as listed above. The above details for formula V and for the preferred compounds of the formula apply here correspondingly.

The alkanones or alkanals used comprise an acetal group.

Preferred alkanones or alkanals having an acetal group are those of the formula VII $$R^2-\overset{O}{\overset{\|}{C}}-(CH_2)_m-CH\overset{OR^8}{\underset{OR^8}{\diagdown}}$$

in which $R^2$ is an H atom or a C1 to C10 alkyl group and m is 0 or an integer from 1 to 10. m corresponds to the m in the above formula III, and has the corresponding definitions and preferred definitions.

$$-CH\overset{OR^8}{\underset{OR^8}{\diagdown}}$$

is the acetal group, and $R^8$ is a hydrocarbon group, more particularly a $C_1$ to $C_{10}$ alkyl group, very preferably a methyl group.

$R^2$ corresponds to the $R^2$ in formula I and has the corresponding definitions and preferred definitions; in one preferred embodiment, $R^2$ is a methyl group.

For the implementation of the addition reaction, the above details relating to stage 1 for the preparation of compounds of the formula I with $R^1$=formula II apply analogously.

Stage 2

In stage 2, the ring closure takes place. Here, the above details regarding stage 3 for the preparation of compounds of the formula I with $R^1$=formula II apply analogously.

Product of the second stage is a compound having a cyclic carbonate group and an acetal group.

Stage 3

In the 3rd stage, ring closure to give the 1,3-dioxane ring takes place. For this purpose, the product of the second stage is reacted with a compound having a total of at least three hydroxyl groups, preferably exactly three hydroxyl groups, with two of the hydroxyl groups being located in 1,3 position. The two hydroxyl groups in 1,3 position form the 1,3-dioxane ring by reaction with the acetal group.

This reaction may be carried out according to customary methods.

The compound having the at least three hydroxyl groups is preferably a compound of the formula VIII

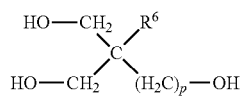

R⁶ and p correspond to R⁶ and p in formula III above, and therefore have the corresponding definitions and preferred definitions.

In particular, the compound of the formula VIII is trimethylolpropane.

The reaction may be carried out in the presence or absence of solvent. Preferably it takes place in the presence of solvent. The solvent in this case is preferably selected such that all of the starting materials are dissolved as completely as possible. In the reaction, the alcohol HO—R⁸ is eliminated, this more particularly being methanol. When a high-boiling solvent such as toluene is used, methanol can easily be removed by distillation. However, the alcohol HO—R⁸, more particularly methanol, may also remain in the reaction mixture; therefore, solvents with a lower boiling point or polar solvents, such as acetonitrile, are also suitable.

The reaction takes place preferably in the presence of catalysts. Examples of suitable catalysts are organic or inorganic acids. As examples, mention may be made of methanesulfonic acid and p-toluenesulfonic acid.

The solvent used in the reaction may optionally be removed prior to further working up. Working up may take place in turn by a phase separation. For this purpose, a suitable solvent is added which dissolves the desired product of the 3rd stage as completely as possible and which is not miscible with water. Examples of solvents contemplated include toluene or MTBE (methyl tert-butyl ether). The organic phase obtained can be washed with water one or more times. The aqueous phase is discarded in each case. The organic phase can be purified by distillation or crystallization.

The 4th stage

In the 4th stage, finally, the compound of the formula I with R¹=formula III is obtained by a transesterification. This 4th stage corresponds to the 4th stage in the preparation of compounds of the formula I with R¹=formula II, but with the difference that in this case the starting compound is not a protected alcohol but rather an unprotected alcohol. Consequently, all relevant details above apply correspondingly.

A schematic representation of the four stages is also found in preparation example 2.2.

In an alternative procedure, it would be possible to change the sequence of the stages and, for example, to reverse the sequence of stages 2 and 3, giving the sequence 1-3-2-4 of the stages above. In that case, the transacetalization of the compound of the formula VIII with the compound of the formula VIII would be carried out first. Preferably in that case the third hydroxyl group of the compound VIII, which is not to take part in the transacetalization, is protected by a protecting group. Only then does the ring closure with $CO_2$ take place.

Preference, however, is given to the above, numerical sequence of the stages, from stage 1, via stage 2, then 3 to stage 4.

Preparation of Compounds of the Formula (I) with R¹=Formula (IV)

Compounds of the formula (I) with R¹=formula (IV) may be prepared in particular by processes in which in a first stage, a compound having a terminal triple bond is reacted with an alkanone or alkanal which comprises an acetal group, the triple bond undergoing addition to the carbonyl group of the alkanone or alkanal to form a hydroxy compound, in a second stage, the ring closure to form the carbonate group takes place with carbon dioxide, in a third stage, the ring closure to form the 1,3-dioxolane ring is carried out by reaction of the acetal group with a compound having a total of at least three hydroxyl groups, with two of the hydroxyl groups being located in 1,2 position, and in a fourth stage, the (meth)acryloyl group is introduced by esterification or transesterification of the remaining hydroxyl group.

These four stages correspond to the four stages in the above-described preparation of compounds of the formula I with R¹=formula III. The above details concerning the preparation of compounds of the formula I with R¹=formula III therefore apply correspondingly, unless stated otherwise below.

The key difference, of course, is in the choice of the compound having the at least three hydroxyl groups in the 3rd stage, since a 1,3-dioxolane ring (five-membered ring) is being prepared, rather than a 1,3-dioxane ring (six-membered ring).

Correspondingly, two of the hydroxyl groups of the compound are in 1,2 position.

One preferred compound having three hydroxyl groups of this kind is glycerol.

Use in Epoxy Resin Compositions

Compounds of the formula (I) are suitable as additives to epoxy resin compositions. In these compositions they act in particular as reactive diluents. Suitable epoxy resin compositions are described in WO 2013/050311 and WO 2011/157671. The compounds of the formula (I) are able to replace the cyclic carbonates described in WO 2013/050311 and WO 2011/157671 in the epoxy resin compositions.

Epoxy resin compositions generally comprise
a) compounds of the formula (I) and
b) compounds having at least one epoxy group (epoxy compounds for short), and
c) optionally hardeners for epoxy compounds, and
d) optionally further constituents.

The compounds of the formula (I)

The compounds of the formula (I) are subject to the statements above. The compounds identified above as being preferred are also preferred in the epoxy resin compositions.

Compounds of the formula I can be comprised in any desired quantities in the epoxy resin compositions. They may be comprised in small amounts, or else in a distinct excess. The possibility of using either deficit or excess quantities of compounds of the formula I is a considerable advantage.

The compound or compounds of the formula I may be used, for example, in a total amount of at least 0.1 part by weight, more particularly at least 0.5 part by weight, more particularly at least 1 part by weight, or of at least 2 or at least 5 parts by weight, based on 100 parts by weight of the epoxy compounds b). The compound or compounds of the formula I may be used in a total amount, for example, of not more than 10 000 parts by weight, preferably not more than 1000 parts by weight, more particularly not more than 200 parts by weight or 100 parts by weight, based on 100 parts by weight of the epoxy compounds b).

The epoxy resin compositions therefore comprise compounds of the formula I more particularly in amounts of, for example, 0.1 to 10 000 parts by weight, preferably of 0.1 to 1000 parts by weight, more preferably of 0.5 to 200 parts by weight per 100 parts by weight of epoxy compounds b).

The Epoxy Compounds

Epoxy compounds contemplated include in particular those which are customarily used in curable epoxy resin compositions. They include, in particular, compounds having 1 to 10 epoxide groups, preferably having at least two epoxide groups in the molecule. The amount of epoxide groups in typical epoxy resins is in the range from 120 to 3000 g/equivalent, calculated as so-called epoxide equivalent in accordance with DIN 16945.

Preferred among these are what are called glycidyl-based epoxy compounds, especially those prepared by etherification of aromatic, aliphatic, or cycloaliphatic polyols with epichlorohydrin. Glycidyl-based epoxy compounds of these kinds are also referred to as polyglycidyl ethers of aromatic, aliphatic, or cycloaliphatic polyols.

The epoxy compounds may be compounds which are liquid at 20° C. and 1 bar (liquid resins for short) or compounds which are solid at 20° C. and 1 bar (solid resins for short), or mixtures of these. Liquid resins differ from solid resins in lower viscosity. Moreover, liquid resins generally have a higher fraction of epoxide groups and, correspondingly, a lower epoxide equivalent.

The amount of epoxide groups in typical liquid resins is customarily in the range from 120 to 200 g/equivalent, and that of the solid resins is in the range of 450-3000 g/equivalent, calculated as so-called epoxide equivalent in accordance with DIN 16945.

The viscosity of liquid resins at 25° C. is customarily in the range from 1 to 20 Pas, preferably in the range from 5 to 15 Pas. The viscosity of the solid resins at 25° C. is customarily in the range of 5 to 40 Pas, preferably in the range from 20 to 40 Pas. The viscosities stated here are the values determined in accordance with DIN 53015 at 25° C. as 40% strength solutions of the resins in methyl ethyl ketone.

Suitable epoxy compounds are, for example, those available commercially under the brand names EPILOX®, EPONEX®, EPIKOTE®, EPONOL®, D.E.R., ARALDIT®, or ARACAST®.

In one preferred embodiment, the epoxy resin is selected from polyglycidyl ethers of aromatic polyols.

Examples thereof are the compounds derived from the diglycidyl ether of bisphenol A (R'=CH3) and the resins derived from bisphenol F (R'=H), these resins being describable through the following general formula:

In the formula, the parameter n indicates the number of repeating units, with the average value of n corresponding with the respective average molecular weight.

The value of n may for example be from 0 to 10.

Examples of epoxy compounds based on polyglycidyl ethers of aromatic polyols are, in addition, glycidyl ethers of phenol- and cresol-based novolaks. Novolaks are prepared by the acid-catalyzed condensation of formaldehyde and phenol or cresol. Reacting the novolaks with epichlorohydrin gives the glycidyl ethers of the novolaks. Also contemplated more particularly are mixtures of different polyglycidyl ethers of aromatic polyols.

In another preferred embodiment of the invention the epoxy compounds is selected from polyglycidyl ethers of cycloaliphatic polyols and from the polyglycidyl esters of cycloaliphatic polycarboxylic acids. Examples of polyglycidyl ethers of cycloaliphatic polyols are the ring-hydrogenation products of polyglycidyl ethers based on bisphenol A, the ring-hydrogenation products of polyglycidyl ethers based on bisphenol F, the ring-hydrogenation products of polyglycidyl ethers based on novolaks, and mixtures thereof. Compounds of these kinds are customarily prepared by selective hydrogenation of the aromatic rings in the aforementioned aromatic polyglycidyl ethers. Examples of such products are P 22-00 from LeunaHarze and Eponex 1510 from Hexion. Exemplary of polyglycidyl esters of cycloaliphatic polycarboxylic acids is diglycidyl hexahydrophthalate.

Also suitable as epoxy compounds for paint formulations are polyacrylate resins containing epoxide groups. These resins are prepared in general by copolymerization of at least one ethylenically unsaturated monomer which comprises at least one epoxide group, more particularly in the form of a glycidyl ether group, in the molecule, with at least one further ethylenically unsaturated monomer that comprises no epoxide group in the molecule, with preferably at least one of the comonomers being an ester of acrylic acid or methacrylic acid. Examples of the ethylenically unsaturated monomers which comprise at least one epoxide group in the molecule are glycidyl acrylate, glycidyl methacrylate, and allyl glycidyl ether. Examples of ethylenically unsaturated monomers which comprise no epoxide group in the molecule are alkyl esters of acrylic and methacrylic acid which comprise 1 to 20 carbon atoms in the alkyl radical, more particularly methyl acrylate, methyl methacrylate, ethyl acrylate, ethyl methacrylate, butyl acrylate, butyl methacrylate, 2-ethylhexyl acrylate and 2-ethylhexyl methacrylate. Other examples of ethylenically unsaturated monomers which comprise no epoxide groups in the molecule are acids, such as acrylic acid and methacrylic acid, for example. Acid amides, such as acrylamide and methacrylamide, for example, vinylaromatic compounds, such as styrene, meth-

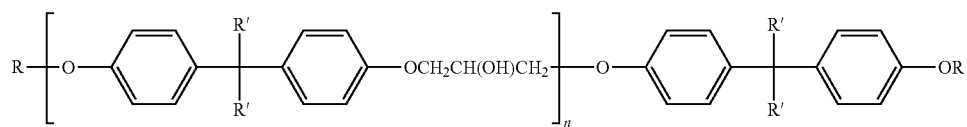

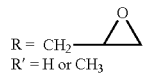

ylstyrene, and vinyltoluene, nitriles, such as acrylonitrile and methacrylonitrile, vinyl halides and vinylidene halides, such as vinyl chloride and vinylidene fluoride, vinyl esters, such as vinyl acetate, for example, and hydroxyl-containing monomers, such as hydroxyethyl acrylate and hydroxyethyl methacrylate, for example. The polyacrylate resin containing epoxide groups customarily has an epoxide equivalent weight of 400 to 2500, preferably 500 to 1500, more preferably 600 to 1200. The number-average molecular weight (determined by gel permeation chromatography using a polystyrene standard) is situated typically in the range from 1000 to 15 000, preferably from 1200 to 7000, more preferably from 1500 to 5000. The glass transition temperature (Tg) is situated typically in the range from 30 to 80° C., preferably from 40 to 70° C., more preferably from 50 to 70° C. (measured by means of differential calorimetry (DSC)). Polyacrylate resins containing epoxide groups are known (cf., e.g., EP-A-299 420, DE-B-22 14 650, DE-B-27 49 576, U.S. Pat. Nos. 4,091,048 and 3,781,379). Examples of such resins are Epon 8021, Epon 8111, Epon 8161 from Hexion.

The epoxy compounds may also derive from other epoxides (nonglycidyl ether epoxy resins). These include, more particularly, compounds, including oligomers and polymers, which have at least one, more particularly two or more, epoxidized cycloaliphatic groups, more particularly 7-oxabicyclo[4.1.0]heptyl groups, which are obtainable by epoxidizing compounds having cyclohexenyl groups. Examples of the epoxidation products of compounds having at least one cycloolefinic group are 4-epoxyethyl-1,2-epoxy-cyclohexane and the compound of the following formula:

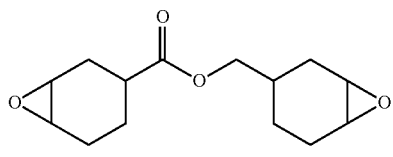

(CAS number 2386-87-0)

which for example is sold by Cytec under the name Uvacure 1500. It is preferred to use the compounds which have at least one, more particularly two or more, epoxidized cycloaliphatic groups, more particularly 7-oxabicyclo[4.1.0] heptyl groups, which are obtainable by epoxidizing compounds having cyclohexenyl groups, and oligomers thereof, not alone but instead in combination with one or more of the aforementioned substances which have at least two glycidyl ether groups in the molecule.

The above epoxy resins can in each case be used as sole epoxy resins or as a mixture.

The Hardeners for Epoxy Compounds

The epoxy resin composition, comprising epoxy resins, one or more compounds of the formula I, and optionally further constituents, is cured by addition of hardeners, which react with the epoxide groups.

The hardeners are preferably compounds having at least one primary or secondary amino group (amino hardeners for short).

Amino hardeners crosslink epoxy resins by reaction of the primary or secondary amino groups with the epoxide groups of the epoxy compounds. Amino hardeners of this kind preferably have at least two amino groups, and generally have 2 to 6, more particularly 2 to 4, amino groups. The amino hardeners may comprise exclusively primary amino groups, exclusively secondary amino groups, or both primary and secondary amino groups.

Customary amino hardeners are, for example, aliphatic polyamines such as ethylenediamine, 1,2- and 1,3-propanediamine, neopentanediamine, hexamethylenediamine, octamethylenediamine, 1,10-diaminodecane, 1,12-diaminododecane, diethylenetriamine, triethylenetetramine, tetraethylene-pentamine, trimethylhexamethylenediamine, 1-(3-aminopropyl)-3-aminopropane, 1,3-bis(3-aminopropyl)propane, 4-ethyl-4-methylamino-1-octylamine, and the like;

cycloaliphatic diamines, such as 1,2-diaminocyclohexane, 1,3-bis(aminomethyl)-cyclohexane, 1-methyl-2,4-diaminocyclohexane, 4-(2-aminopropan-2-yl)-1-methylcyclohexane-1-amine, isophoronediamine, 4,4'-diaminodicyclohexylmethane, 3,3'-dimethyl-4,4'-diaminodicyclohexylmethane, 4,8-diaminotricyclo [5.2.1.0]decane, norbornanediamine, menthanediamine, menthenediamine, and the like;

aromatic diamines, such as tolylenediamine, xylylenediamine, especially meta-xylylenediamine, bis(4-aminophenyl)methane (MDA or methylenedianiline), bis(4-aminophenyl) sulfone (also known as DADS, DDS or dapsone), and the like;

cyclic polyamines, such as piperazine, N-aminoethylpiperazine, and the like;

polyetheramines, especially difunctional and trifunctional primary polyetheramine based on polypropylene glycol, polyethylene glycol, polybutylene oxide, poly(1,4-butanediol), poly-THF or polypentylene oxide, e.g., 4,7,10-trioxatridecane-1,3-diamine, 4,7,10-trioxatridecane-1,13-diamine, 1,8-diamino-3,6-dioxaoctane (XTJ-504 from Huntsman), 1,10-diamino-4,7-dioxadecane (XTJ-590 from Huntsman), 1,12-diamino-4,9-dioxadodecane (BASF SE), 1,3-diamino-4,7,10-trioxatridecane (BASF), primary polyetheramines based on polypropylene glycol having an average molar mass of 230 such as, for example, polyetheramine D 230 (BASF SE) or Jeffamine® D 230 (Huntsman), difunctional, primary polyetheramines based on polypropylene glycol having an average molar mass of 400, e.g., polyetheramine D 400 (BASF SE) or Jeffamine® XTJ 582 (Huntsman), difunctional, primary polyetheramines based on polypropylene glycol having an average molar mass of 2000 such as, for example, polyetheramine D 2000 (BASF SE), Jeffamine® D2000 or Jeffamine® XTJ 578 (Huntsman), difunctional, primary polyetheramines based on propylene oxide having an average molar mass of 4000 such as, for example, polyetheramine D 4000 (BASF SE), trifunctional, primary polyetheramines prepared by reacting propylene oxide with trimethylolpropane followed by an amination of the terminal OH groups, having an average molar mass of 403, such as, for example, polyetheramine T 403 (BASF SE) or Jeffamine® T 403 (Huntsman), trifunctional, primary polyetheramine prepared by reacting propylene oxide with glycerol, followed by an amination of the terminal OH groups, having an average molar mass of 5000, such as, for example, polyetheramine T 5000 (BASF SE) or Jeffamine® T 5000 (Huntsman), aliphatic polyetheramines constructed from a propylene oxide-grafted polyethylene glycol and having an average molar mass of 600, such as, for example, Jeffamine® ED-600 or Jeffamine® XTJ 501 (each Huntsman), aliphatic polyetheramines constructed from a propylene oxide-grafted polyethylene glycol and having an average molar mass of 900, such as, for example, Jeffamine® ED-900 (Huntsman), aliphatic polyetheramines constructed from a propylene oxide-grafted polyethylene glycol and having an average molar mass of 2000, such as, for example, Jeffamine® ED-2003 (Huntsman), difunctional, primary polyetheramine prepared by amination of a propylene oxide-grafted diethylene glycol, having an average molar mass of 220, such as, for example, Jeffamine® HK-511 (Huntsman), aliphatic polyetheramines based on a copolymer of poly(tetramethylene ether glycol) and polypropylene glycol having an average molar mass of 1000 such as, for example, Jeffamine® XTJ-542 (Huntsman), aliphatic polyetheramines based on a copolymer of poly(tetramethylene ether glycol) and polypropylene glycol having an average molar mass of 1900, such as, for example Jeffamine® XTJ-548 (Huntsman), aliphatic polyetheramines based on a copolymer of poly(tetramethylene ether glycol) and polypropylene glycol having an average molar mass of 1400 such as, for example, Jeffamine® XTJ-559 (Huntsman), polyethertriamines based on a butylene oxide-grafted alcohol having a functionality of at least three, having an average molar mass of 400, such as, for example, Jeffamine® XTJ-566 (Huntsman), aliphatic polyetheramines prepared by amination of butylene oxide-grafted alcohols having an average molar mass of 219, such as, for example, Jeffamine® XTJ-568 (Huntsman), polyetheramines based on pentaerythritol and propylene oxide having an average molar mass of 600 such as, for example, Jeffamine® XTJ-616 (Huntsman), polyetheramines based on triethylene glycol having an average molar mass of 148, e.g., Jeffamine® EDR-148 (Huntsman), difunctional, primary polyetheramines prepared by amination of a propylene oxide-grafted ethylene glycol, having an average molar mass of 176, such as, for example, Jeffamine® EDR-176 (Huntsman), and also polyetheramines prepared by amination of PolyTHF having an average molar mass of 250, e.g., PolyTHF-Amine 350 (BASF SE), and mixtures of these amines;

polyamidoamines (amidopolyamines) which are obtainable by reaction of polycarboxylic acids, more particularly dicarboxylic acids such as adipic acid or dimeric fatty acids (e.g., dimeric linoleic acid) with low molecular mass polyamines, such as diethylenetriamine, 1-(3-aminopropyl)-3-aminopropane or triethylenetetramine, or other diamines such as the aforementioned aliphatic or cycloaliphatic diamines, or alternatively are obtainable by Michael addition of diamines with acrylic esters, and subsequent polycondensation of the resulting amino acid esters;

phenalkamines (also phenolalkanamines), meaning phenol or phenol derivatives which are substituted on at least one C atom of the ring system by hydrocarbon groups which comprise primary or secondary amino groups; apart from the hydroxyl group of the phenol or phenol derivative and the primary or secondary amino groups, the phenalkamines comprise no other functional groups. More particularly the phenalkamines comprise both primary and secondary amino groups. Highly suitable phenalkamines comprise preferably a total of 2 to 10, more particularly 2 to 8, and, in one particular embodiment, 4 to 6 such amino groups; phenalkamines in question are preferably those based on cardanol, which is comprised in cashew nut shell oil; cardanol-based phenalkamines are substituted on at least one, preferably on one to three C atoms of the ring system, by above-described, preferably aliphatic hydrocarbon groups comprising primary or secondary amino groups. These substituents are located more particularly in ortho- or para-position to the hydroxyl group; phenalkamines can be prepared by Mannich reaction from the phenol or phenol derivative, an aldehyde, and a compound having at least one primary or secondary amino group. The phenalkamines are therefore Mannich bases or adducts of amino compounds, more particularly one of the above amino compounds, with epoxide compounds; and adducts of amino compounds with epoxide compounds; such adducts are reaction products of epoxide compounds with an excess of amino compounds, such that all of the epoxide groups have undergone reaction and the compounds obtained still have primary or secondary amino groups, and these adducts, therefore, can be used accordingly as amino hardeners. Preferred epoxide compounds here are those having one or two epoxide groups. Amino compounds used for preparing adducts are preferably low molecular weight amino compounds having primary amino groups, more particularly those as described later on below as well as amine compounds H1 (cohardeners). Examples of adducts include the adducts of xylenediamine (MXDA), isophoronediamine (IPDA) or diethylenetriamine with bisphenol A or bisphenol F.

It is also possible to use any desired mixtures of different amino hardeners.

In one preferred embodiment it is possible to use mixtures of the amino hardeners H1 and H2, defined below.

These amino hardeners H1 are also referred to below as cohardeners, while other amino hardeners, not falling within the above definition of the amino hardeners H1, are referred to below as amino hardeners H2.

The amino hardeners H1 (cohardeners)

Amino hardeners H1 are aliphatic, cycloaliphatic or aromatic amine compounds having 1 to 4 primary amino groups and optionally further functional groups selected from secondary amino groups, tertiary amino groups and hydroxyl groups, the primary amino groups in the case of the cycloaliphatic and aromatic amine compounds being bonded in the form of aminomethylene groups (H2N—CH2-) to the cycloaliphatic or aromatic ring system.

Apart from the primary and optionally secondary amino groups, tertiary amino groups or hydroxyl groups, the cohardeners otherwise comprise preferably no other functional groups.

Examples of preferred cohardeners include aliphatic amine compounds which apart from a primary amino group comprise no other functional groups, examples being C2 to C8 alkyleneamines, such as ethylamine, propylamine or butylamine.

Examples of preferred cohardeners also include linear or branched aliphatic amine compounds which comprise two primary amino groups and otherwise no other functional groups, examples being C2 to C8 alkylenediamines, such as ethylenediamine, propylenediamine or butylenediamine.

Examples of preferred cohardeners also include aliphatic amine compounds which comprise one or two primary amino groups and one or two hydroxyl groups and otherwise no other functional groups, examples being monoamines, such as C2 to C8 alkanolamines, such as ethanolamine and isopropanolamine.

Examples of preferred cohardeners also include aliphatic amine compounds which comprise a primary amino group and a tertiary amino group and otherwise no other functional groups. Examples include compounds of the formula

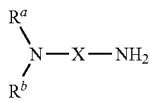

In the above formula, Ra and Rb independently of one another are a C1 to C10, preferably a C1 to C4, alkyl group. X is a C2 to C10, preferably a C2 to C4, alkylene group. The alkylene group may be branched or linear; it is substituted at any desired location by the tertiary and the primary amino group. In one preferred embodiment the alkylene group is linear and substituted terminally by the tertiary and primary amino group. An example of one of the particularly preferred cohardeners here is 3-dimethylaminopropylamine (DMAPA).

Preferred cohardeners are also aliphatic amine compounds which comprise one or two primary amino groups, preferably one primary amino group, and one secondary amino group and one hydroxyl group, and otherwise no other functional groups. These are more particularly N-(2-aminoalkyl)alkanolamines, e.g., N-(2-aminoethyl)ethanolamine (H2N—CH2-CH2-NH—CH2-CH2-OH). The two alkylene groups in these compounds preferably have consist of 2 to 8 C atoms.

Examples of preferred aromatic cohardeners also include benzene substituted by one to three aminomethylene groups (H2N—CH2-). This more particularly is benzene substituted by two H2N—CH2- groups at any desired position of the benzene ring, e.g., xylenediamine with the formula

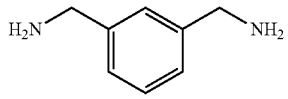

Examples of preferred cycloaliphatic cohardeners also include cyclohexane substituted by one to three aminomethylene groups (H2N—CH2-). More particularly this is cyclohexane which is substituted by two H2N—CH2- groups at any desired position of the benzene ring.

Also contemplated, of course, are any desired mixtures of the above cohardeners.

The cohardeners preferably have a molecular weight of less than 500 g/mol, more particularly less than 300 g/mol.

Preferred cohardeners are composed in total of a maximum of 10 C atoms; particularly preferred cohardeners are composed in total of a maximum of 8 C atoms.

Of the cohardeners identified above, the aliphatic compounds are preferred; particularly preferred aliphatic compounds are those having only one primary amino group and optionally one tertiary amino group or optionally one hydroxyl group and otherwise no other functional group.

The weight fraction of the cohardeners is preferably from 2% to 40% by weight, more preferably from 5% to 35% by weight, based on the weight total of all amino hardeners.

The cohardeners are used preferably in amounts of 0.1 to 30 parts by weight, more preferably in amounts of 0.5 to 20 parts by weight, based on epoxy compounds.

The amino hardeners used in addition to the cohardeners are amino hardeners H2 which do not fall within the above definition of the cohardeners, as set out above. The fraction of these amino hardeners H2 is then, correspondingly, preferably 60% to 98% by weight, more preferably 65% to 95% by weight, based on the weight total of all amine hardeners.

Examples of amino hardeners H2 of these kinds include polyamidoamines, phenalkamines, epoxy-amine adducts, polyetheramines or other amino compounds different from the amino hardeners H1 (cohardeners), or mixtures thereof.

The amino hardeners H2 are preferably polyamidoamines, phenalkamines, epoxy-amine adducts, polyetheramines or mixtures thereof.

If mixtures of different amino hardeners are used, they may be mixed beforehand and then added as a mixture to the epoxy resin composition, or else they may also be added separately. They can also be added simultaneously or in conjunction with other constituents of the epoxy resin composition. Examples of such constituents contemplated include the additives identified above.

The total amount of amino hardener required for curing, or weight total of all amino hardeners H1 and H2, is determined in a manner known per se via the number of epoxide groups in the formulation and the number of functional groups in the hardener. The number of epoxide groups in the epoxy resin is specified as the so-called epoxide equivalent. The epoxide equivalent is determined in accordance with DIN 16945.

The number of primary and secondary amino groups can be calculated via the amine number in accordance with DIN 16945.

The amino hardeners are preferably used in total in amounts such that the ratio of the number of all primary and secondary amino groups to the number of all epoxide groups in the epoxy resin is 2:1 to 1:2, preferably 1.5:1 to 1:1.5, and more particularly 1.1:1 to 1:1.1. At a stoichiometric ratio of about 1:1, a cured resin with optimum thermoset properties is obtained. Depending on the desired properties of the resin after crosslinking, however, it may also be useful to use hardener and epoxy resin in other ratios of the reactive groups.

In the epoxy resin compositions, accordingly, the total amount of amino hardeners (weight total of H1 and H2) is generally 0.1% by weight to 50% by weight, frequently 0.5% to 40% by weight, and more particularly 1% to 30% by weight, based on the weight total of epoxy compounds, compounds of the formula I, and amino hardeners H1 and H2.

Besides amino hardeners there may also be other hardeners used as well, e.g., anhydride hardeners. In one preferred embodiment, however, compounds amino hardeners exclusively are used.

Further constituents of the epoxy resin composition

Besides the epoxy resins and the compounds of the formula I, the epoxy resin compositions may further comprise other diluents, including other reactive diluents.

Examples of other reactive diluents are low molecular weight compounds with a molecular weight of preferably not more than 250 daltons, in the range from 100 to 250 daltons, for example, that have oxirane groups, preferably glycidyl groups, in the form of glycidyl ether groups, glycidyl ester groups or glycidylamide groups, for example.

Other reactive diluents include, for example, glycidyl ethers of saturated alkanols having 2 to 20 C atoms, or alkoxylated alkanols.

In one particular embodiment the epoxy resin compositions comprise no reactive diluents other than the above compounds of the formula I. If other reactive diluents are used as well, the weight ratio of the compound of the formula I to other reactive diluents may be for example in the range from 1:10 to 10:1, more particularly in the range from 1:5 to 5:1.

The epoxy resin compositions may further also comprise nonreactive organic diluents. These are understood to mean organic solvents which under atmospheric pressure have a boiling point below 200° C. and which do not enter into any bond-forming reaction with the epoxide groups and with the groups of any reactive diluent present, and which escape in the course of the subsequent use. Examples include aliphatic, cycloaliphatic or aromatic hydrocarbons, alcohols, ketones or esters.

In one preferred embodiment the epoxy resin compositions comprises nonreactive organic solvents at most in minor amounts (less than 20% by weight, in particular less than 10% by weight or less than 5% by weight, based on the weight total of epoxy resin and compound of the formula I) and with particular preference they comprise no such solvent (100% system).

Besides the aforementioned constituents, the epoxy resin composition may comprise fillers and/or other additives which are desired for the particular use of the epoxy resin compositions.

Examples of suitable fillers include inorganic or organic particulate materials such as, for example, calcium carbonates and silicates and also inorganic fiber materials such as glass fibers, for example. Organic fillers such as carbon fiber and mixtures of organic and inorganic fillers, such as, for example, mixtures of glass and carbon fibers or mixtures of carbon fibers and inorganic fillers, may also be employed. The fillers may be added, for example, in an amount of 1% to 70% by weight, based on the total weight of the epoxy resin composition.

Suitable conventional additives comprise, for example, antioxidants, UV absorbers/light stabilizers, metal deactivators, antistats, reinforcing agents, fillers, antifogging agents, blowing agents, biocides, plasticizers, lubricants, emulsifiers, colorants, pigments, rheological agents, impact tougheners, catalysts, adhesion regulators, optical brighteners, flame retardants, antidropping agents, nucleating agents, flow control agents, and defoamers.

Further constituents of the epoxy resin compositions, and/or of a separate hardener mixture, include catalysts that accelerate the curing reaction, examples being phosphonium salts of organic or inorganic acids, imidazole and imidazole derivatives, tertiary amino compounds such as triethanolamine or triisopropanolamine, or quaternary ammonium compounds. Such other catalysts are used, if desired, in fractions of 0.01% to about 10% by weight, based on the total weight of the epoxy resin, the compound I, and total amount of the amino hardeners. In one preferred embodiment, no such catalysts are needed, meaning that the amount of such catalysts in the composition is less than 0.5%, more particularly less than 0.1% or less than 0.01% by weight.

The Use of the Epoxy Resin Compositions

In epoxy resin compositions, a fundamental distinction is made between one-component (1K) and two-component (2K) binder systems. With 2K systems, epoxy compounds and hardeners remain separate until shortly before curing (hence 2-component), since the epoxy resin and the hardener are highly reactive. With 2K systems, the hardener is not added until shortly before curing to the epoxy compound or to the epoxy resin composition.

The epoxy resin compositions of the invention are more particularly 2K systems.

The addition of the hardeners, preferably of a hardener mixture comprising at least one hardener, preferably at least one amino hardener, takes place, accordingly, not until shortly before use.

The two-component epoxy resin composition therefore comprises a separate epoxy resin composition, which comprises epoxy resins, compounds of the formula I, and optionally other constituents, but no hardeners, more particularly no amino hardener, and a separate hardener mixture, which comprises hardeners, preferably amino hardeners, but no epoxy compounds.

The 2K systems therefore comprise a system composed of a component A, comprising
  a) compounds of the formula (I) and
  b) compounds having at least one epoxy group (epoxy compounds for short), and a component B, comprising
  c) hardeners for epoxy compounds.

Both A and B may comprise further constituents, especially the further constituents stated above.

The hardener mixture more preferably comprises a mixture of amino hardeners H1 and H2 and optionally other constituents, for example, catalysts (see above).

After the hardeners have been added to the epoxy resin composition, curing takes place.

Curing may then take place thermally by heating of the composition. The curing of the epoxy resin compositions takes place customarily at temperatures in the range from −10 to 200° C., preferably in the range from −10 to 180° C., and more particularly in the range from −10 to 150° C.

Alternatively, curing may also take place, for example, with microwave induction. Curing takes place more particularly at −10 to 80° C., and in one particularly preferred embodiment at −10 to 40° C. or at −10 to 20° C. An advantageous feature is that the curing can take place under standard ambient conditions such as room temperature and/or sunlight exposure.

The epoxy resin compositions are used as 1K or 2K systems in a diversity of technical applications, irrespective of whether they are 1K or 2K systems.

They are suitable, for example, as coating compositions, casting compositions, for producing composite materials, as adhesives, more particularly as structural adhesive, or for impregnating fibers or fiber fabrics. In these uses they can be used as sole binders or else in combination with other binders.

Coating compositions include, for example, paints. With the epoxy resin compositions of the invention, it is possible for example to obtain scratch-resistant protective paint coatings on any desired substrates, composed of metal, plastic or woodbase materials, for example.

Since the reactivity of the epoxy resin compositions is comparatively high, curing can be effected at low temperatures, as for example in the range from 0 to 50° C. and more particularly in the range from 5 to 35° C. This makes the epoxy resin compositions especially suitable for the coating of substrates of very large surface area, which cannot be heated, or can be heated only with difficulty, to temperatures above the ambient temperature. This includes in particular the coating of floors, particularly in highly trafficked areas, as for example for the coating of traffic areas in public buildings or squares, or for the coating of parking areas and access points of parking areas. Particularly included here as well is the coating of large-surface-area metal components and metal constructions, such as in or on buildings or boats (marine coating), for example.

The epoxy resin compositions are also suitable as insulating coatings in electronic applications, as an insulating coating for wires and cables, for example. Their use for producing photoresists may also be mentioned. They are especially suitable, too, as repair paint material, in connection, for example, with the repair of pipes without pipe disassembly (cure in place pipe (CIPP) rehabilitation). They are suitable as well for the sealing and coating of floors.

As casting compositions for embedding, attaching or consolidating moldings, the epoxy resin compositions can be used, for example, in electronic applications. They are suitable as flip-chip underfill or as electrical casting resins for potting, casting, and (glob-top) encapsulation.

The epoxy resin compositions are especially suitable also for producing composite materials. In composite materials (composites), different materials, examples being plastics and reinforcing materials (fibers, carbon fibers), are joined to one another through the cured epoxy resin.

The epoxy resin compositions are also suitable as adhesives, especially structural adhesives. Structural adhesives serve for the permanent joining of shaped parts to one another. The shaped parts may be made of any desired material; materials contemplated include plastic, metal, wood, leather, ceramic, etc. The adhesives may also be hot melt adhesives, which are fluid and processable only at a relatively high temperature. They may also be flooring adhesives. The compositions are also suitable as adhesives for producing printed circuit boards (electronic circuits), not least by the SMT (surface mounted technology) method.

The epoxy resin compositions are suitable, for example, for producing impregnated fibers or for producing preimpregnated yarns and fabrics produced from fibers, as for example for producing prepregs which are processed further into composites. Production methods for composites include the curing of preimpregnated fibers or fiber fabrics (e.g., prepregs) after storage, or else the extrusion, pultrusion, winding, and resin transfer molding (RTM) and resin infusion (RI) technologies. In particular, the fibers and/or the yarns and fabrics produced from them may be impregnated with the composition of the invention and thereafter cured at an elevated temperature.

The epoxy resin composition is suitable more particularly for methods, such as the coating of surfaces, impregnation, shaping or the like, for example, in which the epoxy resin composition is applied to the surface that is to be coated, or is introduced into the desired mold, and is subsequently cured. These methods are not subject to any restrictions in terms of the surface to be coated. Examples of suitable surfaces are metal surfaces, wood surfaces, glass surfaces, plastics surfaces.

In accordance with the preparation processes described above, compounds of the formula I are available easily and in good yields. They are extremely suitable, for example, as reactive diluents in epoxy resin compositions.

Particular advantages that may be stated for the epoxy resin compositions include the low viscosity through accompanying use of compounds of the compounds of the formula I, and the good performance properties, including more particularly the very good elasticity. Compounds of the formula I can be used in either small or large amounts in the epoxy resin compositions.

EXAMPLES

1. Materials

ExoVC Acrylate 1:

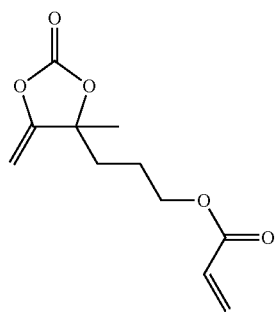 [SMILES: C=CC(=O)OCCCC1(C)OC(=O)OC1=C]

ExoVC Acrylate 2:

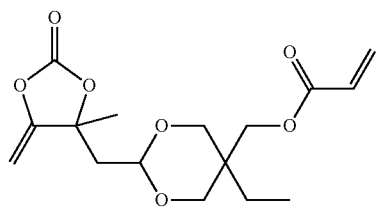 [SMILES: C=CC(=O)OCC1(CC)COC(CC2(C)OC(=O)OC2=C)OC1]

ExoVC, Comparative

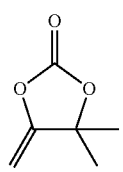

4,4-Dimethyl-5-methylene-1,3-dioxolan-2-one (ExoVC for Short) According to WO2011/157671

Epoxy Resin:
Aromatic epoxy resin based on bisphenol A with an epoxide equivalent of 175-185 g/eq and with a viscosity at 25° C. of 8-10 Pa·s (Epilox A 18-00)
Hardeners
Hardener H1: Polyetheramine D230 (BASF SE)
Hardener H2: Isophoronediamine (IPDA, BASF SE)

2. Preparation Examples 2.1. Preparation of ExoVC Acrylate 1
The preparation takes place in four stages.
The reaction scheme below encompasses stages 1 to 3

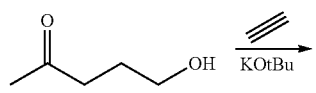

-continued

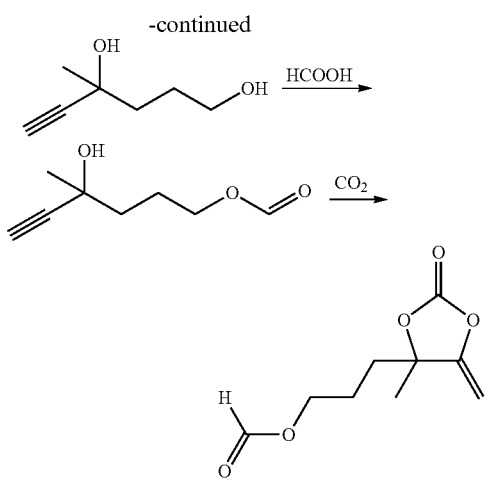

1st Stage: Reaction of Hydroxypentanone with Acetylene to Give the Acetylene Adduct:

KOtBu (800 g, 7.1 mol) is introduced in anhydrous THF (4.5 L) and cooled to 0-3° C. Acetylene (280 g, 10.8 mol) is introduced at this temperature over the course of 3 hours. Then, with further introduction of acetylene (130 g, 5 mol), hydroxypentanone (550 g, 5.39 mol) is added dropwise at 0-6° C. over the course of 1 hour. After passage through a viscosity maximum, an orange-brown solution is formed here.

After 1 hour of subsequent stirring at 0-3° C., the system is warmed to RT and, at 20-25° C., ammonium chloride (1068 g in 5 L of water) is added over the course of 45 minutes. Two phases are formed.

The organic phase is separated off, dried over sodium sulfate, and stripped of its solvent on a rotary evaporator at 40° C. and 5 mbar.

649 g of a brown oil are obtained. This oil is distilled under an oil pump vacuum, observing a liquid-phase temperature of not more than 130° C. The principal fraction was obtained at 110-111° C. in the form of a yellow oil (440 g, 3.4 mol, 64%).

Purity (GC area %): 93%

2nd Stage: Reaction of the Diol with Formic Acid to Give the Formate:

The diol obtained in the first stage (1.305 kg, 10.2 mol) is introduced and is admixed with formic acid (1.512 L, 40 mol) at 7-8° C. over the course of 1 hour. The system is then warmed to room temperature and the progress of the reaction is observed by GC/FID. The reaction is allowed to continue until there is virtually no longer any increase in the principal peak, this being the case after about 4 hours at RT. If the reaction is continued beyond this point, there is increased formation of doubly formylated product.

For working up, the reaction mixture is first concentrated under reduced pressure, without heating, and the crude product obtained is then distilled at 12 mbar. The principal fraction goes over at 112-115° C. in the form of a clear yellow liquid (1.453 kg, 9.3 mol, 91%). Purity (GC area %): 93%

3rd Stage: Ring Closure with $CO_2$ to Give the ExoVC Formate

The formate obtained in the second stage (1.623 kg, 10.4 mol) is admixed with silver acetate (1.38 g) and TMTACN (N,N',N"-trimethyl-1,4,7-triazacyclononane, 13.8 mL) and subjected to 10 bar of $CO_2$ in a stirred autoclave with a pressure maintenance valve.

Over the course of 5 hours, the temperature rises to 56° C. and the pressure to 18 bar. When the temperature has dropped back to RT, the mixture is heated to 70° C. The pressure at this stage rises to about 28 bar. After about 4 hours, reaction monitoring shows virtually no remaining reactant (GC/FID).

The system is cooled and let down. The contents of the autoclave are admixed with dichloromethane (1.5 L) and then washed twice with HCl (10% strength solution, 480 mL each time) and dried over sodium sulfate, and the solvent is removed on a rotary evaporator (40° C., 60 mbar).

Thereafter, with stirring at RT, all of the constituents volatile under an oil pump vacuum are removed, a procedure which may take up to 48 hours. About 1.9 kg of crude product are obtained.

For further purification, volatile components are first separated off in a thin-film evaporator with wiper system (0.05-0.02 mbar, jacket temperature 109-114° C.). At least two runs are usually required for this purpose.

Then, in a further run, the target compound is separated off from low-volatility constituents (0.012 mbar, jacket temperature 170° C.).

Yield of ExoVC formate: 1.419 kg (7.1 mol, 68%).

Purity (GC area %): 97%

4th Stage: Acrylation to Give the ExoVC Acrylate 1

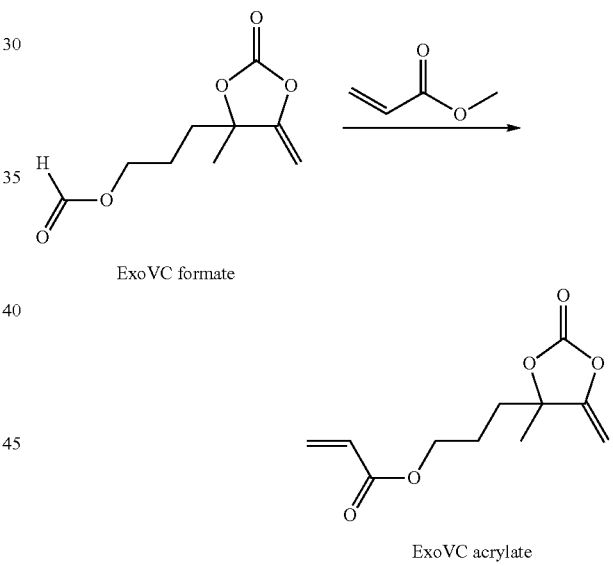

A two-liter flat-bottom flask with Teflon stirrer, thermometer and condenser was charged with 300 g of ExoVC formate (1.5 mol) and 1200 g of methyl acrylate (14 mol). The methyl acrylate contained 0.3 g of MeHQ (monomethyl ether of hydroquinone) as inhibitor. The mixture was stirred and heated to 40° C. 30 g of the enzyme Candida Antarctica lipase B (immobilized form) were added.

After 24 hours, the resulting mixture was decanted into a two-liter round-bottom flask, with the enzyme remaining in the flat-bottom flask. The methanol formed and, simultaneously, methyl acrylate were removed under reduced pressure.

The residue was returned, together with 1000 g of fresh methyl acrylate, to the flat-bottom flask containing the enzyme. The mixture obtained was stirred again at 40° C. for 24 hours.

The reaction mixture was cooled to room temperature and filtered. Methanol and unreacted methyl acrylate were removed by distillation under reduced pressure.

The yield was 339 g of ExoVC acrylate 1

Purity: 96.7% (determined by gas chromatography)

2.2 Preparation of ExoVC Acrylate 2

The preparation takes place in four stages.

The reaction scheme below encompasses stages 1 to 3

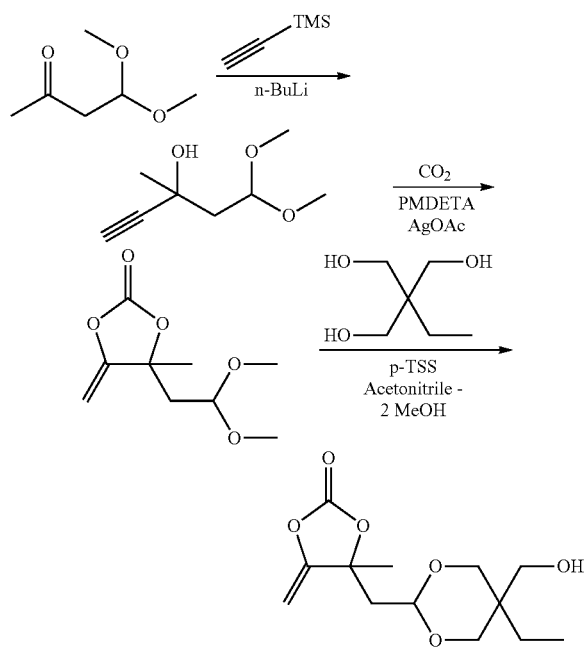

1.) Ethynylation of 4,4-dimethoxybutan-2-one

TMS-acetylene (982 g, 10 mol) is initially charged under argon in THF (17 L, dried over molecular sieve) and cooled to −68° C. With stirring, over the course of 1 h, n-butyllithium (2.5 M in hexane, 4 L) is added dropwise at −68° C., followed by stirring for a further hour.

Over the course of 30 minutes, the ketone (1.319 kg, 10 mol) is then added dropwise at −68° C. to −54° C., followed by stirring for 15 minutes. After that, the mixture is heated to 9° C. and water (2.9 L) is added in one portion. The temperature here rises to about 17° C.

The reaction mixture is concentrated thoroughly at 45° C./8 torr. GC analysis ensures that there is no longer any TMS-protected product present.

The residue is suspended in diethyl ether (750 mL) and filtered, and the filtration residue is washed again with diethyl ether. The filtrate is concentrated under reduced pressure. This leaves about 1.2 kg of crude material as a brown liquid.

By vacuum distillation (5 mbar), about 1.1 kg (7 mol, 70%) of ethynylated product are obtained from the brown liquid at 64-68° C., in the form of a colorless oil.

Purity: >96% (GC area %)

2.) Ring Closure with $CO_2$

The acetylene alcohol (1233 g; 7.79 mol) obtained in stage 1 is introduced in acetonitrile (1.2 L) and admixed in a stirred autoclave with PMDETA (pentamethyldiethylenetriamine; 138.9 g; 0.8 mol) and AgOAc (12.9 g; 0.078 mol). 50 bar of $CO_2$ are injected and the mixture is stirred for 2.5 hours. The temperature rises to 75° C.

After cooling to room temperature, the reaction mixture is let down to atmospheric pressure, filtered, and concentrated at 100° C./5 mbar. About 1.5 g of crude material remain, in the form of a brown liquid.

By vacuum distillation at 5 mbar, about 1.39 kg of the carbonate are obtained as an orange-colored oil from the brown liquid, at 114-115° C., and this oil crystallizes to completion overnight (possibly after addition of a few seed crystals).

The crystal mass is stirred with cyclohexane (1.34 L), and filtered with suction, and the residue is washed again with cyclohexane (0.45 L).

Drying under reduced pressure gives 1.29 kg (6.38 mol, 64%) of almost colorless solid.

Purity: >99% (GC area %)

3.) Transacetalization with Trimethylolpropane

The dimethoxy-substituted carbonate from stage 2 (250 g, 1.24 mol) is introduced in 1.4 L acetonitrile under an argon atmosphere. Then 253 g (1.87 mol) of trimethylolpropane and 407 mg (0.002 mol) of p-toluenesulfonic acid hydrate are added. The mixture is heated under reflux for 10 hours.

After cooling to room temperature, the solvent is removed under reduced pressure and the residue is taken up in about 1 L of MTBE. It is washed with four times 300 mL of water. The organic phase is dried over sodium sulfate, filtered, and concentrated on a rotary evaporator. This is followed by drying at 40° C. under an oil pump vacuum for several hours.

The product is obtained as a viscose, slightly yellowish oil (339 g) in the form of two isomers, this oil slowly crystallizing on prolonged standing at room temperature.

Purity: >98% (GC area %)

4.) Acrylation to Give ExoVC Acrylate 2

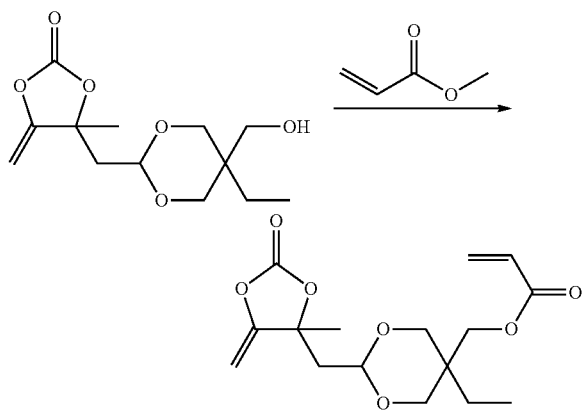

In a two-liter flat-bottom flask with Teflon stirrer, thermometer, and condenser, 129 g of ExoVC-PMP alcohol (0.47 mol), 409 g of methyl acrylate (4.75 mol), and 152 g of molecular sieve 5 Å powder were introduced. The methyl acrylate contained 0.3 g of MeHQ (monomethyl ether of hydroquinone) as inhibitor. The mixture was stirred and heated to 60° C. 9.7 g of the enzyme *Candida Antarctica* lipase B (immobilized form) were added.

After 72 hours, 100 g of molecular sieve 5 Å powder and 9.7 g of the enzyme *Candida Antarctica* lipase B (immobilized form) were added.

After 96 hours, the reaction mixture was cooled to room temperature and filtered. Methanol and unreacted methyl acrylate were removed by distillation under reduced pressure.

The yield was 153 g of ExoVC acrylate 2.

Purity: 97.1% (determined by gas chromatography)

3. Performance Tests

The epoxy resin compositions were prepared by mixing the epoxy resins, the hardeners, and the reactive diluents (ExoVC acrylate 1, ExoVC acrylate 2 or ExoVC). The tables give the details of the epoxy resins, hardeners and reactive diluents used and also of their parts by weight.

3.1 Viscosity and Reactivity

The initial viscosity of the epoxy resin compositions was determined at 25° C. using a plate/plate viscometer having a slot width of 1 mm (MCR302, Anton Paar).

Using the same instrument, the increase in the viscosity of the compositions was measured over time (temperature 25° C.). The tables report the time taken for the initial viscosity to double. The shorter the time, the higher the reactivity.

3.2 Glass Transition Temperature Tg

The glass transition temperature $T_g$ of the epoxy resin compositions was determined by DSC (Differential Scanning calorimetry) in accordance with ASTM 3418/82.

3.3 Cupping test (DIN EN ISO1520)

The elasticity of coatings on a metallic substrate is determined using the cupping test. A steel sheet was coated with the epoxy resin compositions (film thickness 100 μm). The coated metal sheet was stored at room temperature overnight. In an apparatus for performing the cupping test, the sheet was deformed by forceful application of a die to the uncoated side, causing the coated side to bulge out correspondingly. The height of the bulge at which cracks are observed in the coating for the first time is a measure of the elasticity. The higher the bulge at the first cracks, the more elastic the coating. The values reported in the table are average values from three measurements.

3.4 Shore D Hardness

The epoxy resin compositions were placed, in an amount of 10 g, into dishes having a radius of 4 cm, and stored at 25° C. for 7 days. For the determination of the Shore D hardness, a defined needle with defined length is pressed completely into the coating. The Shore D hardness corresponds to the force required to achieve this. The tables report the average values from 5 measurements. The greater the force, the higher the hardness.

TABLE 1

Initial viscosity and reactivity

| No. | Epoxy resin parts by weight | Diluent type | Diluent parts by weight | Hardener type | Hardener parts by weight | Initial viscosity mPas | Reactivity min |
|---|---|---|---|---|---|---|---|
| 1 | 10 | — | 0 | H1 | 3.4 | 577 | 180 |
| 2 | 9 | ExoVC acrylate1 | 1 | H1 | 4.0 | 340 | 28 |
| 3 | 7 | ExoVC acrylate1 | 3 | H1 | 5.3 | 310 | 9.8 |
| 4 | 5 | ExoVC acrylate1 | 5 | H1 | 6.8 | 125 | 4.2 |
| 5 | 3 | ExoVC acrylate1 | 7 | H1 | 8.0 | 80 | 3 |
| 6 | 9 | ExoVC acrylate2 | 1 | H1 | 3.7 | 565 | 41 |
| 7 | 7 | ExoVC acrylate2 | 3 | H1 | 4.5 | 521 | 13.6 |
| 8 | 5 | ExoVC acrylate2 | 5 | H1 | 5.2 | 236 | 6.1 |
| 9 | 3 | ExoVC acrylate2 | 7 | H1 | 5.9 | 187 | 4.1 |
| 10 | 9 | ExoVC | 1 | H1 | 4.0 | 236 | 25.2 |
| 11 | 10 | — | 0 | H2 | — | 2540 | 40 |
| 12 | 10 | ExoVC acrylate1 | 0.5 | H2 | 2.4 | 3000 | 34.4 |
| 13 | 10 | ExoVC acrylate1 | 0.5 | H2 | 2.6 | 2413 | 30.6 |
| 14 | 10 | ExoVC acrylate1 | 0.5 | H2 | 2.7 | 2515 | 36.6 |
| 15 | 10 | ExoVC acrylate1 | 1 | H2 | 2.7 | 2657 | 13.4 |
| 16 | 10 | ExoVC | 1 | H2 | 2.5 | 1700 | 8.5 |

TABLE 2

Cupping test and Shore hardness of the hardened epoxy resin compositions

| No. | Epoxy compound parts by weight | Diluents type | Diluents parts by weight | Hardener type | Hardener parts by weight | Tg ° C. | Cupping test mm | Shore D hardness |
|---|---|---|---|---|---|---|---|---|
| 1 | 10 | — | 0 | H1 | 3.4 | 92.6 | 0.6 | 89.5 |
| 2 | 9 | ExoVC acrylate1 | 1 | H1 | 4.0 | 69.9 | 9.0 | 89.0 |
| 3 | 7 | ExoVC acrylate1 | 3 | H1 | 5.3 | 41.8 | 9.0 | 86.6 |
| 4 | 5 | ExoVC acrylate1 | 5 | H1 | 6.8 | 24.7 | 9.0 | 76.9 |
| 5 | 3 | ExoVC acrylate1 | 7 | H1 | 8.0 | — | 9.0 | 36.9 |
| 6 | 9 | ExoVC acrylate2 | 1 | H1 | 3.7 | 74.8 | 0.7 | 88.4 |
| 7 | 7 | ExoVC acrylate2 | 3 | H1 | 4.5 | 53.7 | 0.9 | 87.6 |
| 8 | 5 | ExoVC acrylate2 | 5 | H1 | 5.2 | 33.8 | 9.0 | 86.5 |

TABLE 2-continued

Cupping test and Shore hardness of the hardened epoxy resin compositions

| No. | Epoxy compound parts by weight | Diluents type | parts by weight | Hardener type | parts by weight | Tg °C. | Cupping test mm | Shore D hardness |
|---|---|---|---|---|---|---|---|---|
| 9 | 3 | ExoVC acrylate2 | 7 | H1 | 5.9 | 22.5 | 9.0 | 77.7 |
| 10 | 9 | ExoVC | 1 | H1 | 4.0 | 62.5 | 0.5 | 88.2 |

What is claimed is:

1. A compound of formula (I)

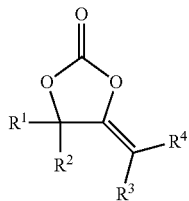

(I)

in which
$R^1$ is an organic radical having a (meth)acryloyl group and $R^2$, $R^3$, and $R^4$ independently of one another are an H atom or a C1 to C10 alkyl group.

2. The compound according to claim 1, wherein $R^1$ is an organic radical having a total of not more than 24 C atoms and comprising no heteroatoms other than oxygen atoms.

3. The compound according to claim 1, wherein $R^1$ is a group of formula (II)

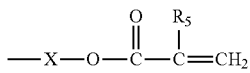

(II)

in which X is a bond or an alkylene group having 1 to 18 C atoms and $R^5$ is an H atom or a methyl group, or $R^1$ is a group of formula (III)

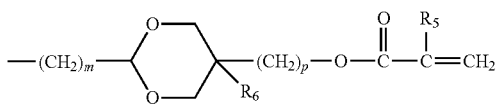

(III)

in which m and p independently of one another are 0 or an integer from 1 to 10, $R^5$ is an H atom or a methyl group, and $R^6$ is an H atom or a C1 to C10 alkyl group, or $R^1$ is a group of formula (IV)

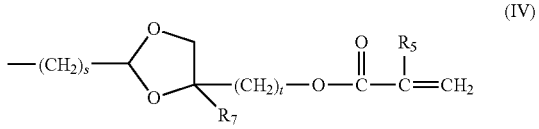

(IV)

in which s and t independently of one another are 0 or an integer from 1 to 10, $R^5$ is an H atom or a methyl group, and $R^7$ is an H atom or a C1 to C10 alkyl group.

4. The compound according to claim 1, wherein $R^2$ is a methyl group and $R^3$ and $R^4$ are an H atom.

5. A process for preparing the compound of claim 3, in which $R^1$ is a group of the formula (II), comprising:
reacting, in a first stage, a compound having a terminal triple bond with a hydroxyalkanone or hydroxyalkanal, the triple bond undergoing addition to the carbonyl group of the hydroxyalkanone or hydroxyalkanal to form a dihydroxy compound,
protecting, in a second stage, the hydroxyl group of the dihydroxy compound that did not originate from the carbonyl group with a protecting group,
ring closing, in a third stage, to form a carbonate group with carbon dioxide, and
replacing, in a fourth stage, the protecting group with a (meth)acryloyl group.

6. A process for preparing the compound of claim 3, in which $R^1$ is a group of the formula (III), comprising:
reacting, in a first stage, a compound having a terminal triple bond with an alkanone or alkanal which comprises an acetal group, the triple bond undergoing addition to the carbonyl group of the alkanone or alkanal to form a hydroxy compound,
ring closing, in a second stage, to form a carbonate group with carbon dioxide,
ring closing, in a third stage, to form a 1,3-dioxane ring by reaction of the acetal group with a compound having a total of at least three hydroxyl groups, with two of the hydroxyl groups being located in 1,3 position, and
introducing, in a fourth stage, the (meth)acryloyl group by esterification or transesterification of the remaining hydroxyl group.

7. A process for preparing the compound of claim 3, in which $R^1$ is a group of the formula (IV), comprising:
reacting, in a first stage, a compound having a terminal triple bond with an alkanone or alkanal which comprises an acetal group, the triple bond undergoing addition to the carbonyl group of the alkanone or alkanal to form a hydroxy compound,
ring closing, in a second stage, to form a carbonate group with carbon dioxide,
ring closing, in a third stage, to form a 1,3-dioxolane ring by reaction of the acetal group with a compound having a total of at least three hydroxyl groups, with two of the hydroxyl groups being located in 1,2 position, and
introducing, in a fourth stage, the (meth)acryloyl group by esterification or transesterification of the remaining hydroxyl group.

8. An epoxy resin composition comprising the compound of claim 1.

9. An epoxy resin composition comprising
a) a compound of claim 1,
b) an epoxy compound having at least one epoxy group
c) optionally a hardener for the epoxy compound, and
d) optionally a further constituent.

10. The epoxy resin composition according to claim 9, comprising 0.1 to 10 000 parts by weight of the compound of the formula (I) per 100 parts by weight of the epoxy compound.

11. The epoxy resin composition according to claim 9, wherein the hardener is present, and has at least one primary or secondary amino group.

12. A two-component binder system comprising:
a component A comprising
a) the compound of claim 1,
b) an epoxy compound having at least one epoxy group, and
a component B comprising
c) a hardener for the epoxy compound.

13. A coating material, casting material, or adhesive comprising the epoxy resin composition of claim 9.

\* \* \* \* \*

UNITED STATES PATENT AND TRADEMARK OFFICE
CERTIFICATE OF CORRECTION

PATENT NO. : 10,407,534 B2
APPLICATION NO. : 15/567513
DATED : September 10, 2019
INVENTOR(S) : Verena Mormul et al.

Page 1 of 1

It is certified that error appears in the above-identified patent and that said Letters Patent is hereby corrected as shown below:

In the Specification

In Column 28, Line 4, delete "calorimetry)" and insert -- Calorimetry) --, therefor.

Signed and Sealed this
Twenty-fourth Day of March, 2020

Andrei Iancu
*Director of the United States Patent and Trademark Office*